United States Patent [19]
Berg et al.

[11] Patent Number: 4,989,598
[45] Date of Patent: Feb. 5, 1991

[54] NEGATIVE PRESSURE FULL FACE RESPIRATOR HAVING A REPLACEABLE VIEWING WINDOW

[75] Inventors: Richard C. Berg, Bloomington; Emil J. Kvaal, North St. Paul, both of Minn.

[73] Assignee: Minnesota Mining and Manufacturing Company, St. Paul, Minn.

[21] Appl. No.: 439,288

[22] Filed: Nov. 20, 1989

[51] Int. Cl.$^5$ ............................................. A62B 18/08
[52] U.S. Cl. ........................................ 128/206.23; 2/8
[58] Field of Search .................... 128/206.23, 206.24, 128/206.21, 206.12, 201.22, 201.23, 201.24, 201.25, 201.27, 201.28, 206.28; 2/8, 15, 429, 434, 435, 441

[56] References Cited
U.S. PATENT DOCUMENTS

| | | | |
|---|---|---|---|
| 2,631,285 | 3/1953 | Maillart | 2/8 |
| 3,220,408 | 11/1965 | Silverberg | 128/206.23 |
| 3,278,943 | 10/1966 | Manz | 2/8 |
| 3,315,673 | 4/1967 | Morton | 128/206.23 |

Primary Examiner—Edgar S. Burr
Assistant Examiner—Stephen R. Funk
Attorney, Agent, or Firm—Donald M. Sell; Walter N. Kirn; David W. Anderson

[57] ABSTRACT

A full face negative pressure respirator having a replaceable viewing window is described. The respirator is especially useful as a welder's negative pressure full face respirator where the viewing window is subject to chipping and/or scratching that can impair the vision of the wearer. The full face negative pressure respirator of the present invention utilizes a viewing window insert assembly that comprises an integrally molded curved insert wall and viewing window chamber that accommodates easy replacement of an optically damaged viewing window while providing a gas tight seal between the viewing window and the insert assembly which is not subject to failure by an increase in negative pressure within the facial cavity of the respirator during normal use conditions.

14 Claims, 2 Drawing Sheets

NEGATIVE PRESSURE FULL FACE RESPIRATOR HAVING A REPLACEABLE VIEWING WINDOW

FIELD OF THE INVENTION

The present invention relates to a full face negative pressure respirator having a replacable viewing window and more specifically to a full face negative pressure respirator used by welders.

BACKGROUND INFORMATION

Safety regulations require that personnel working in a hazardous environment must be protected from that environment. Frequently the hazard is a direct result of a specific activity, such as welding, and the activity may produce multiple hazards. Typical hazards which welders are exposed to include electrical shock, ultraviolet light, hazardous fumes and gases resulting from the welding operation and projectile hazards produced when slag and weld spatter is chipped from the workpiece. In so far as possible, it is desirable to provide a single safety device that will comfortably and conveniently provide necessary protection to the worker. U.S. Pat. No. 2,631,285 (Maillart) describes a glass holder intended to be molded into the face shield of a welder's helmet. The holder consists essentially of an outer metallic frame and an inner molded insert, the molded insert being adapted to be mounted in the window opening of the face shield of a welder's helmet. The metallic frame has an inwardly extending flange which defines the window opening therein and against which a glass pane is pressed by a rectangular spring which is in a wide V-shape. The spring is backed by the molded insert from which it may be quickly released.

SUMMARY OF THE INVENTION

The present invention provides a negative pressure respirator adapted to cover at least the mouth, nose and eyes of a wearer comprising a soft compliant face sealing member having at least one inhalation valve, an exhalation valve and a harness assembly for holding the respirator tightly against the face of a wearer. A filtration element capable of removing hazardous fumes and gases is removably attached to the inhalation valve by means of a gas tight seal. The respirator further comprises a viewing window assembly which is peripherally engaged by the face sealing member by means of a gas tight seal. The viewing window insert assembly comprises a panel having an outer periphery and a centrally located opening with a wall structure extending outwardly from one face of the panel along its outer periphery. The panel and wall structure combine to define a viewing window chamber within the wall structure with the panel as its bottom face and its top face being open to the atmosphere. A resilient gasket material, which is coextensive with the face of the panel, is secured to the panel within the window viewing chamber. A viewing window is removably positioned against the gasket material and is kept in position over the opening in the panel by positioning means which are located between the opening and the wall structure and are symmetrically disposed around the opening on the face of the panel within the viewing chamber. At least one retaining element is attached to the wall structure within the viewing chamber above the panel at a distance greater than the combined thickness of the viewing window and gasket material. A window retaining means, which forces the viewing window against the gasket material, is disposed between the retaining element and the viewing window. The viewing window chamber is intersected by a curved insert partition that is concave relative to the bottom face of the viewing chamber and is adapted to be received by the face sealing element to form a gas tight seal. When the respirator is positioned on the face of a wearer, the viewing window is disposed opposite the face of the wearer with respect to the gasket material so that a negative pressure within the respirator resulting from inhalation by the wearer produces an additional force against the viewing window, forcing it against the gasket material.

DETAILED DESCRIPTION OF THE INVENTION

Figure 3:
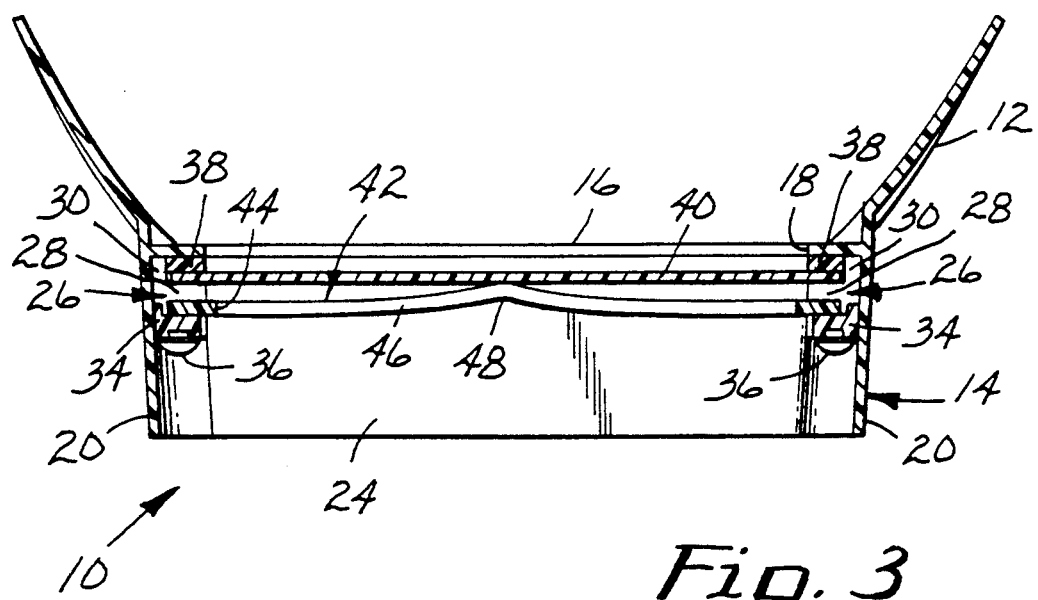
FIG. 3 is a cross-sectional view of the viewing window assembly of FIG. 1 taken generally along the line 3—3 of FIG. 1 with a gasket material, viewing window and retaining spring in position.

Full face protective headgear for welders must protect the welder from electrical shock, ultraviolet light, and hazardous gases as well as providing eye protection from metal chips and welding slag that are produced when the welder chips metal spatter and slag from the workpiece. The full face protective headgear must also be designed so that the welder has a good field of vision, freedom of movement, and the ability to temporarily reposition the ultraviolet light protection means while chipping welding slag and spatter from the workpiece without removing or adversely affecting the respiratory protection provided by the headgear. Additionally, it is highly desirable that the viewing window be designed so that it can be readily replaced once it has become optically damaged.

Two approaches which have been utilized to provide respiratory protection to the welder have been to supply pressurized breathing air to the headgear from a remote source or to utilize a tightly fitting full face respirator which draws ambient air through filter elements that remove hazardous fumes and gases from the air as the wearer inhales and creates a negative pressure (i.e., a pressure less than ambient) in the facial cavity between the interior surface of the respirator and the wearer's face.

Either approach requires a mounting means for the viewing window which provides a substantially gas tight seal between the window and the mounting frame so that the welder is not exposed to hazardous fumes or gases as a result of leaks around the window.

When a remote pressurized air supply is utilized concern about leakage around the window is minimized because the positive pressure within the facial cavity between the respirator and the wearer's face will produce an outward flow of air through a leak around the viewing window, keeping hazardous fumes or gases away from the wearer.

However, leaks around the viewing window in a negative pressure full face respirator pose a very significant risk to the wearer. Negative pressure within the facial cavity between the respirator and the wearer's face created by the wearer inhaling to draw air through filter cartridges can create an inward flow of contaminated air through a leak, thereby introducing hazardous fumes or gases directly into the facial chamber.

One solution to the leak problem in a negative pressure, full face respirator is to permanently mount and seal the viewing window to the respirator body. While offering a functional solution to the leak problem, the economic ramifications of this solution are very poor. Pitting of the viewing window to a level such that it impairs vision typically results in the whole respirator be replaced rather than replacing a far less costly viewing window.

Attempts to adapt conventional replaceable viewing window assemblies, such as that described in U.S. Pat. No. 2,631,285, to a negative pressure full face respirator have been largely unsuccessful. Perhaps one of the main reasons for these failures lies in the fact that viewing window frames similar to that described in U.S. Pat. No. 2,631,285 place the viewing window on the face or internal side of the respirator where it is held against a flange of the assembly only by a retaining spring. In this configuration the viewing window can be forced away from a flange or gasket material by an increase in negative pressure within the facial cavity or by an increase in the ambient air pressure, thereby exposing the wearer to contaminated air.

The full face negative pressure respirator of the present invention utilizes a novel viewing window insert assembly that differs from prior insert assemblies in that the viewing window is positioned externally with respect to the facial cavity and therefore on the atmospheric side of the respirator. In this configuration, forces generated by a low negative pressure within the facial cavity or a high external ambient air pressure, work in concert with the viewing window retaining means to force the window against the gasket material to improve the seal rather than to break it, thereby minimizing the chance of a leak occurring. Higher than normal negative pressure in the facial cavity can be produced when the pressure drop across a filter cartridge is too high, as can occur when the cartridge becomes heavily loaded with particulate materials. Excessive atmospheric pressures acting on the atmospheric side of viewing window can occur as a result of explosions. In either case, the viewing window insert assembly of the present invention provides a level of safety protection to the wearer that far exceeds that provided by previous designs of full face respirators having a replaceable viewing window.

The viewing window insert assembly used in the full face negative pressure respirator of the present invention is advantageously prepared by an injection molding process wherein the viewing window chamber and the concave insert partition are integrally formed in a single operation. Integral formation of the two elements provides a cost effective manufacturing process which minimizes leak possibilities that might occur if individual components were used to assemble the insert assembly. It is contemplated that either a thermoplastic or thermoset injection molding process would be suitable for preparing the insert assembly, although a thermoplastic insert molding process would be preferred as material costs can be lower and molding cycle times shorter. A variety of electrically insulating high temperature performance thermoplastic resins are suitable for preparing the viewing window insert assembly, including, but not limited to, polyamides, polycarbonates, polysulfones and polyimides.

Figure 1:
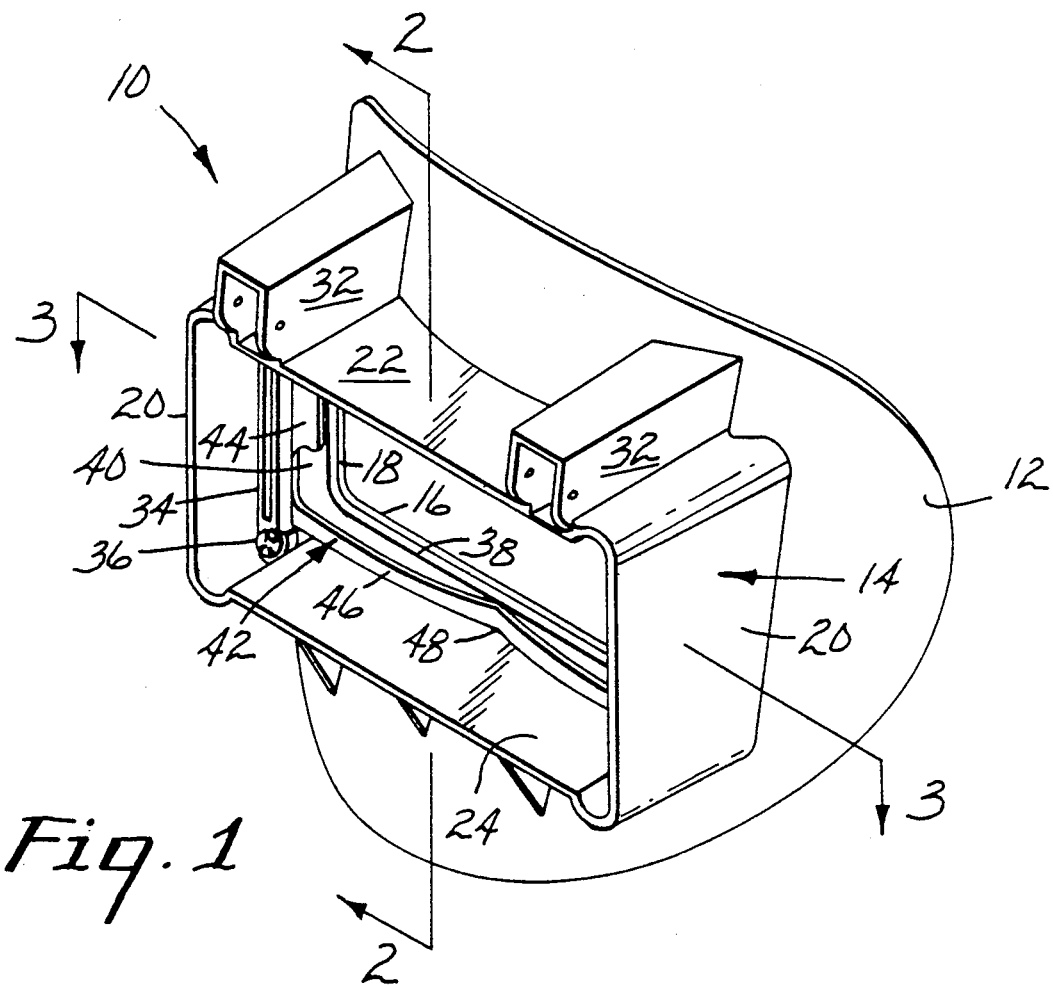
FIG. 1 is a perspective view of the viewing window insert assembly of the present invention.
Figure 2:
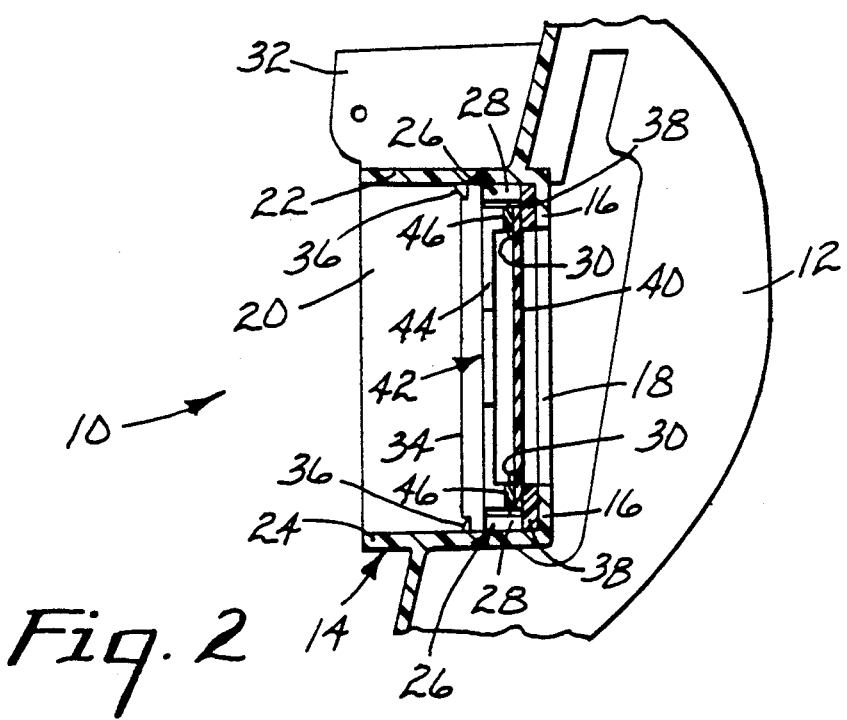
FIG. 2 is a cross-sectional view, rotated 90°, of the viewing window assembly of FIG. 1 taken generally along the line 2—2 of FIG. 1 with a gasket material, viewing window and retaining spring in position.

FIGS. 1-3 are illustrations of the viewing window insert assembly, generally indicated as 10, of the present invention. With primary reference to FIG. 1, the curved insert partition 12 intersects and is integrally molded to the rectangular viewing chamber 14 which is defined by a panel 16 having a centrally located opening 18 and a wall structure including transverse walls 20, an upper longitudinal wall 22 and a lower longitudinal wall 24. Transverse walls 20 and longitudinal walls 22 and 24 can extend from about 2.8 to about 3.3 cm (about 1.1 to 1.3 inches) beyond a plane defined by panel 16, but preferably they should extend no more than about 3.0 cm (about 1.2 inches) beyond the plane of panel 16 so as to not adversely impact the wearer's field of vision. Corner abutments 26, comprising intersecting longitudinal abutments 28 and transverse abutments 30, are located on the face of panel 16 in each corner and engage the viewing window 40 (FIGS. 2 and 3) to keep it centrally positioned over the opening 18 in panel 16. Longitudinal abutments 28 extend further from panel 16 than transverse elements 30 to provide an attachment site for transverse retaining clips 34 (FIGS. 2 and 3). Preferably longitudinal abutments 28 extend approximately twice as far from panel 16 as transverse abutments 30. Hinge mounts 32 are located on upper longitudinal wall 22 to provide an attachment site for pivotally mounting a second window housing (not shown) that can carry a replaceable ultraviolet light blocking viewing window.

FIG. 2 is an illustration of the viewing window insert assembly 10 along line A—A of FIG. 1. Insert partition 12 is concave with respect to panel 16 of viewing chamber 14 to minimize the profile of insert assembly 10 and is angled with respect to viewing window chamber 14 to provide room to accommodate the wearer's nose within the facial chamber of the full face respirator while providing a comfortable viewing angle. Preferably insert partition 12 intersects transverse walls 20 at an angle of from about 10°-20°, and more preferably at an angle of about 15°, relative to longitudinal walls 22 and 24.

Retaining element 34 is secured to adjacent longitudinal abutments 28 along transverse wall 20 by attachment means 36, which includes, but is not limited to mechanical attachment means such as screws, rivets and the like, adhesive attachment means and thermomechanical attachment means such as ultrasonic bonding.

Gasket material 38 is secured to and is coextensive with the face of panel 16 within viewing window chamber 14. Gasket material 38 comprises a resilient material and preferably comprises a closed cell foam material having a Shore 00 durometer of from about 30 to about 70, and more preferably a Shore 00 durometer of from about 45 to about 55. A variety of closed cell materials including, but not limited to polyurethane based materials, polyester based materials and silicone based materials are suitable for use as gasket material 38, with silicone based materials being preferred.

Viewing window 40 comprises a panel of an optically clear material, including, but not limited to glass, poly(meth)acrylate, polystyrene and polycarbonate. Viewing window 40 is sized to fit between corner abutments 26 which position window 40 over centrally located opening 18 in panel 16.

Viewing window 40 is held against gasket material 38 by a removable window securing means 42 to allow easy replacement of viewing window 40. Window securing means 42 can comprise a number of devices, including, but not limited to, leaf springs, resilient tubing, etc. In FIG. 2, window securing means 42 consists of a rectangular shaped leaf spring comprising flat transverse elements 44 and longitudinal elements 46 that have a V-shape. As illustrated in FIGS. 2 and 3, transverse element 44 of the leaf spring is inserted beneath retaining element 34 with apex 48 of V-shaped longitudinal element 46 of the spring facing engaging viewing window 40, urging it against gasket material 38 to create a gas tight seal between window 40 and gasket material 38.

Concave insert partition 12 is adapted to be received by a soft, conformable face sealing member of a full face respirator so as to provide a gas tight seal between the insert panel and the resilient face piece member.

Figure 4:
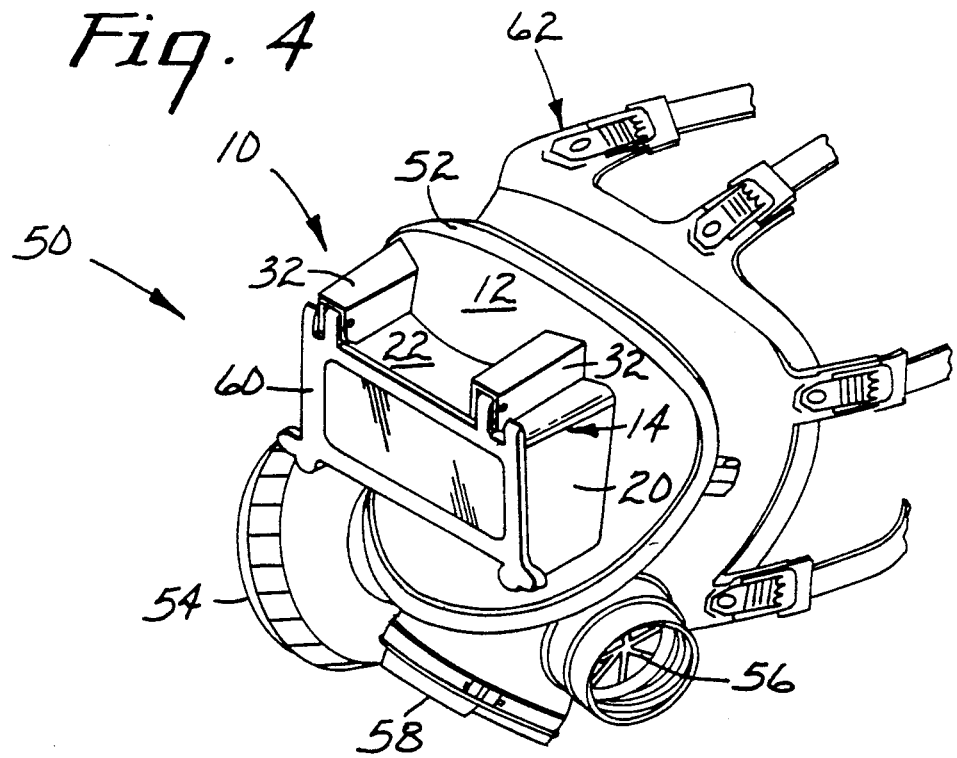
FIG. 4 is a perspective view of a full face negative pressure respirator of the present invention.

FIG. 4 illustrates a full face negative pressure respirator 50 including viewing window insert assembly 10. Respirator 50 comprises insert assembly 10, resilient face sealing member 52, filter cartridges 54, inhalation valve 56 exhalation valve 58, pivotally mounted viewing window assembly 60 for a ultraviolet blocking viewing window and harness assembly 62.

While the negative pressure respirator of the present invention has been described by only one embodiment it is anticipated that variations of the various components of the respirator would be apparent to one skilled in the art.

For example, while viewing window chamber 14 preferably has a rectangular shape, circular or oval shaped viewing window chambers are contemplated as being equally functional in the full face negative pressure respirator of the present invention. Similarly, window opening 18 in panel 16 preferably has a rectangular shape but other shapes such as oval or circular openings would be equally functional.

Positioning means for keeping viewing window 40 centrally located over opening 18 have been described as corner abutments 26 which are preferred for a rectangular viewing window. It is contemplated that a wide variety of other positioning means could be equally functional in keeping viewing window 40 correctly positioned over opening 18. Alternative positioning means would include a continuous or discontinuous ridge-like structure on the panel face within the viewing chamber which is displaced from opening 18 or, panel 16 might be molded with a recess around opening 18 that is slightly larger than opening 18 into which window 40 could be inserted. Another positioning means which is contemplated is the incorporation of spring like members on viewing window 40 which would abut against the wall structure of viewing chamber 14 to keep window 40 positioned over opening 18.

We claim:

1. A negative pressure respirator adapted to cover at least the mouth, nose and eyes of a wearer comprising;
    a soft, conformable face sealing member having an exhalation valve and an inhalation valve;
    a harness assembly attached to said face sealing member, said harness assembly being capable of holding said face sealing member tightly against the face of a wearer;
    a filtration element capable of removing hazardous fumes and gases from inhaled air, said filtration element removably attached to said inhalation valve by means of a gas tight seal, said respirator being a negative pressure respirator in that respiration of said wearer causes a pressure within said respirator which is lower than ambient pressure;
    a viewing window insert assembly, said insert assembly being peripherally engaged by said face sealing member by means of a gas tight seal, said viewing window insert assembly comprising;
    a panel having an outer periphery and a centrally located opening;
    a wall structure extending outwardly from one face of said panel around said panel opening, said wall structure and said panel defining a viewing window chamber within said wall structure, said panel comprising a bottom face of said chamber, the top face of said chamber being open to the atmosphere;
    a resilient gasket material coextensive with and secured to said panel within said viewing window chamber;
    a viewing window removably positioned against said gasket material in said viewing window chamber;
    positioning means for keeping said viewing window located over said opening in said panel, said positioning means being located between said opening and said wall structure and disposed around said opening on the face of said panel within said chamber;
    at least one retaining element attached to said wall structure within said chamber, said element being positioned above said panel at a distance greater than the combined thickness of said viewing window and said gasket material;
    window retaining means for forcing said viewing window against said gasket material, said window retaining means disposed between said viewing window and said retaining element; and,
    wherein, when said respirator is positioned on the face of a wearer, said viewing window is disposed opposite the face of the wearer with respect to said gasket material so that a negative pressure within said respirator resulting from inhalation of the wearer produces an additional force against said viewing window, forcing it more tightly against said gasket material.

2. The negative pressure respirator of claim 1 wherein said viewing window chamber comprises a substantially rectangular shaped chamber.

3. The negative pressure respirator of claim 2 wherein said wall structure extends from about 2.8 to 3.3 cm (about 1.1 to 1.3 inches) beyond the plane defined by said panel.

4. The negative pressure respirator of claim 3 wherein said wall structure extends about 3 cm (about 1.2 inches) beyond the plane defined by said panel.

5. The negative pressure respirator of claim 2 wherein said positioning means comprises abutments located in the corners of said viewing window chamber.

6. The negative pressure respirator of claim 1 wherein said resilient gasket material comprises a closed cell foam.

7. The negative pressure respirator of claim 6 wherein said closed cell foam comprises a silicone foam.

8. The negative pressure respirator of claim 7 wherein said silicone foam has a Shore 00 durometer of from about 30 to about 70.

9. The negative pressure respirator of claim 8 wherein said silicone foam has a Shore 00 durometer of from about 45 to about 55.

10. The negative pressure respirator of claim 5 wherein said at least one retaining element comprises two retaining clips, each clip bridging adjacent corner abutments along a transverse wall within said viewing window chamber.

11. The negative pressure respirator of claim 2 wherein said viewing window retaining means comprises a rectangular shaped leaf spring comprising transverse and longitudinal members, said longitudinal members having an open V-shape.

12. The negative pressure respirator of claim 1 wherein said viewing window insert assembly comprises a thermoplastic resin.

13. The negative pressure respirator of claim 12 wherein said thermoplastic resin is selected from electrically insulating high temperature performance thermoplastic resins including polyamides(i.e. nylons), polycarbonates, polysulfones and polyimides.

14. The negative pressure respirator of claim 1 wherein said viewing window insert assembly comprises a thermoset resin.

* * * * *